(12) United States Patent
Darois et al.

(10) Patent No.: US 9,504,549 B2
(45) Date of Patent: Nov. 29, 2016

(54) FABRIC PROSTHESIS FOR REPAIRING A TISSUE WALL DEFECT IN PROXIMITY OF A TUBE-LIKE STRUCTURE

(75) Inventors: Roger E. Darois, Foster, RI (US); Kathleen Hoye, Boston, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 13/286,929

(22) Filed: Nov. 1, 2011

(65) Prior Publication Data

US 2012/0253366 A1    Oct. 4, 2012

Related U.S. Application Data

(60) Provisional application No. 61/413,073, filed on Nov. 12, 2010.

(51) Int. Cl.

| | | |
|---|---|---|
| *A61F 2/02* | (2006.01) | |
| *A61F 2/00* | (2006.01) | |
| *A61B 17/12* | (2006.01) | |
| *A61B 17/00* | (2006.01) | |

(52) U.S. Cl.
CPC .......... *A61F 2/0063* (2013.01); *A61B 17/0057* (2013.01); *A61B 17/12* (2013.01); *A61B 17/12013* (2013.01); *A61F 2/0009* (2013.01); *A61F 2/0077* (2013.01); *A61F 2002/0068* (2013.01)

(58) Field of Classification Search
USPC ......... 623/11.11, 23.72, 23.73, 23.74, 23.75, 623/23.76; 606/151, 155, 213, 215; 600/37
See application file for complete search history.

(56) References Cited

U.S. PATENT DOCUMENTS

| | | | |
|---|---|---|---|
| 4,769,038 A | | 9/1988 | Bendavid et al. |
| 5,356,432 A | | 10/1994 | Rutkow et al. |
| 5,697,978 A | | 12/1997 | Sgro |
| 5,769,864 A | * | 6/1998 | Kugel ........................... 606/151 |
| 6,174,320 B1 | * | 1/2001 | Kugel et al. .................. 606/151 |
| 6,258,124 B1 | * | 7/2001 | Darois et al. .............. 623/14.13 |
| 6,497,650 B1 | | 12/2002 | Nicolo |
| 6,610,006 B1 | | 8/2003 | Amid et al. |
| 6,652,595 B1 | | 11/2003 | Nicolo |
| 6,736,823 B2 | | 5/2004 | Darois et al. |
| 6,736,854 B2 | | 5/2004 | Vadurro et al. |
| 7,011,688 B2 | | 3/2006 | Gryska et al. |

(Continued)

FOREIGN PATENT DOCUMENTS

WO    WO 2013/048272 A1    4/2013

OTHER PUBLICATIONS

International Search Report and Written Opinion from PCT Application No. PCT/US2011/058811 mailed Feb. 21, 2012.

*Primary Examiner* — Robert Lynch
(74) *Attorney, Agent, or Firm* — Wolf, Greenfield & Sacks, P.C.

(57) ABSTRACT

Implantable prostheses for repairing soft tissue defects near an anatomical tube and methods for their manufacture are described. Exemplary prostheses may be implanted at a soft tissue repair site, for example, in treating an inguinal hernia. An implantable prosthesis may include a patch made up of two co-knit fabric layers, and a passageway for receiving an anatomical cord extending through the fabric layers. The passageway is configured through the first fabric layer so as to minimize the prospects of the cord-like structure contacting the portion of the second fabric layer defining the passageway therethrough. The passageway through the first fabric layer may include a barrier.

20 Claims, 12 Drawing Sheets

(56) References Cited

U.S. PATENT DOCUMENTS

| | | |
|---|---|---|
| 7,101,381 B2 | 9/2006 | Ford et al. |
| 7,156,804 B2 | 1/2007 | Nicolo |
| 7,785,334 B2 | 8/2010 | Ford et al. |
| 7,806,905 B2 | 10/2010 | Ford et al. |
| 8,298,290 B2 | 10/2012 | Pélissier et al. |
| 8,323,675 B2 | 12/2012 | Greenawalt |
| 2002/0052654 A1 | 5/2002 | Darois et al. |
| 2003/0083543 A1 | 5/2003 | Nicolo |
| 2003/0187516 A1 | 10/2003 | Amid et al. |
| 2005/0113849 A1 | 5/2005 | Popadiuk et al. |
| 2006/0064175 A1 | 3/2006 | Pelissier et al. |
| 2008/0124400 A1 | 5/2008 | Liggins et al. |
| 2010/0286716 A1 | 11/2010 | Ford et al. |

\* cited by examiner

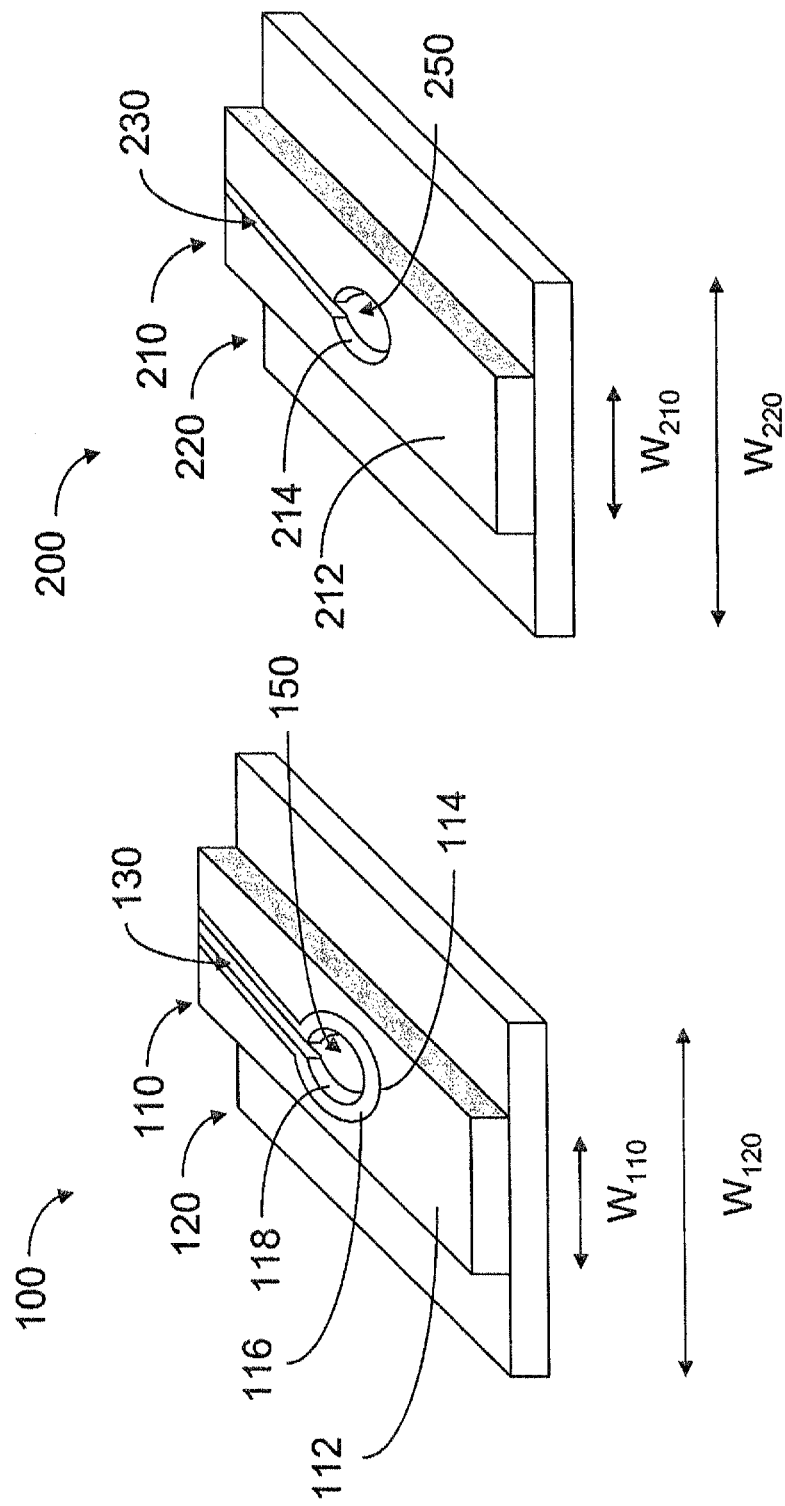

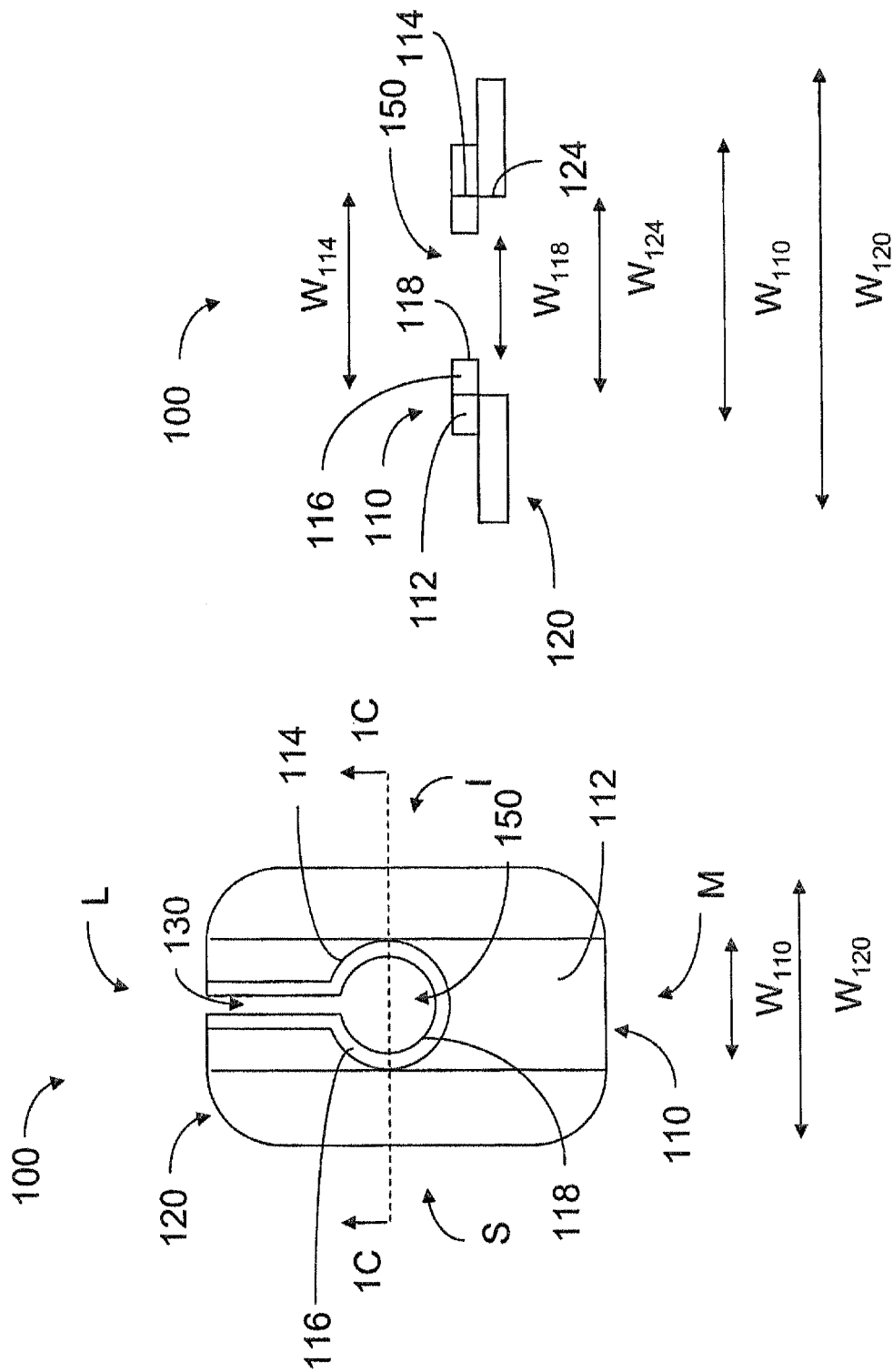

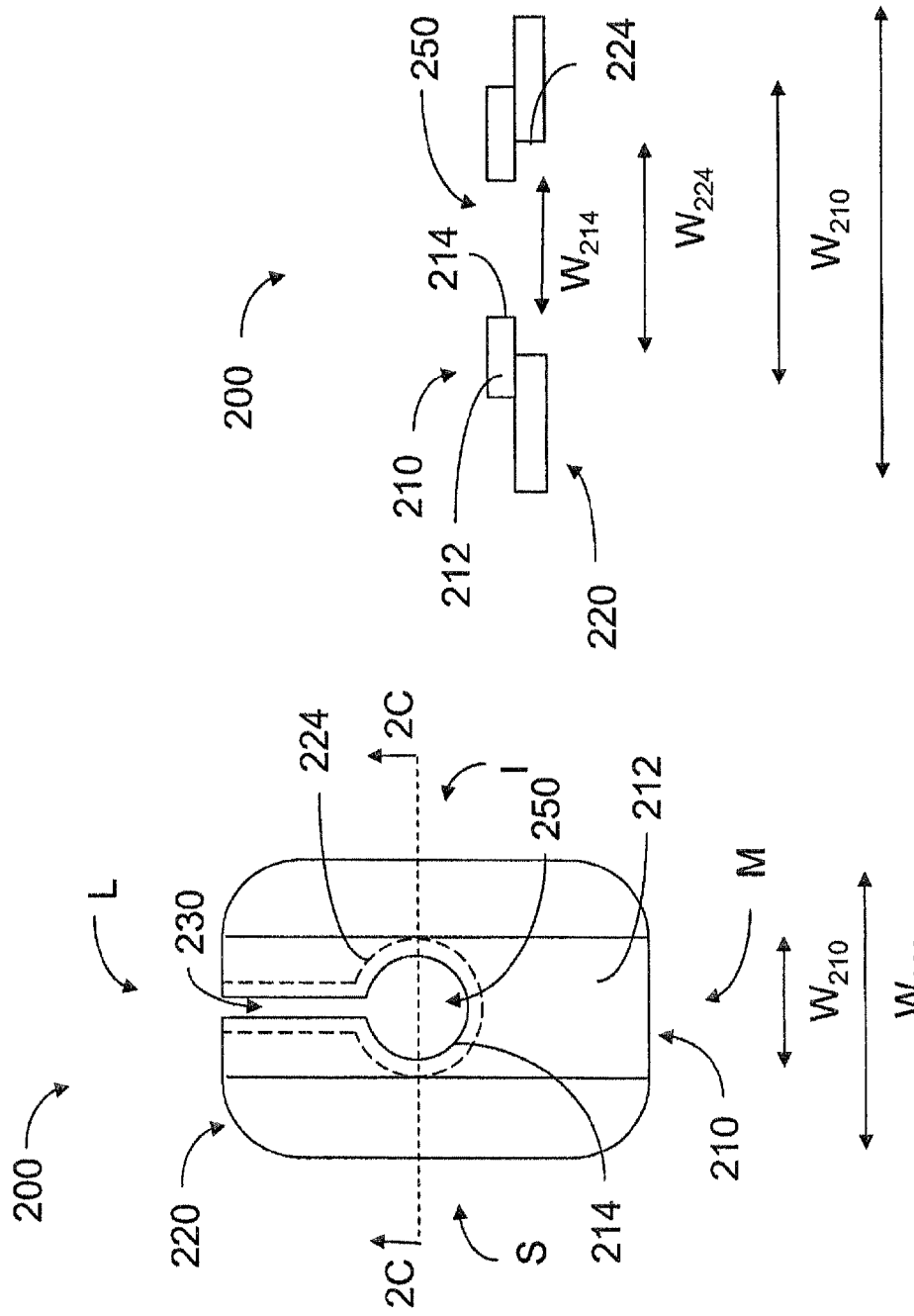

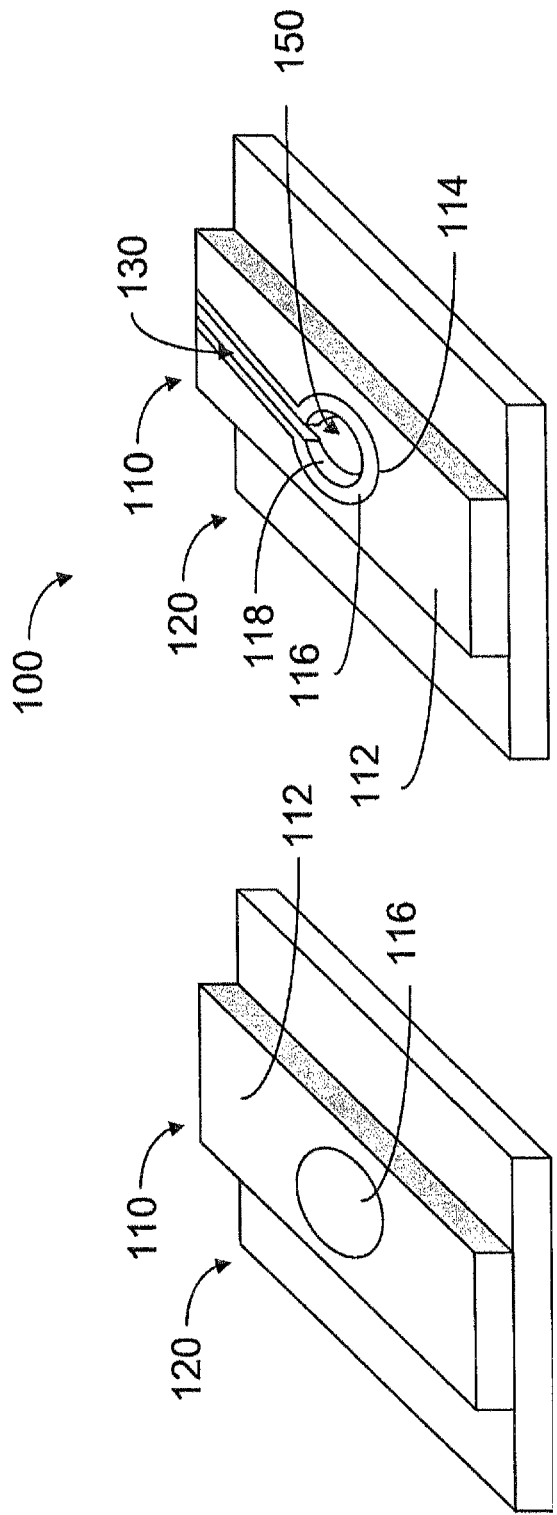

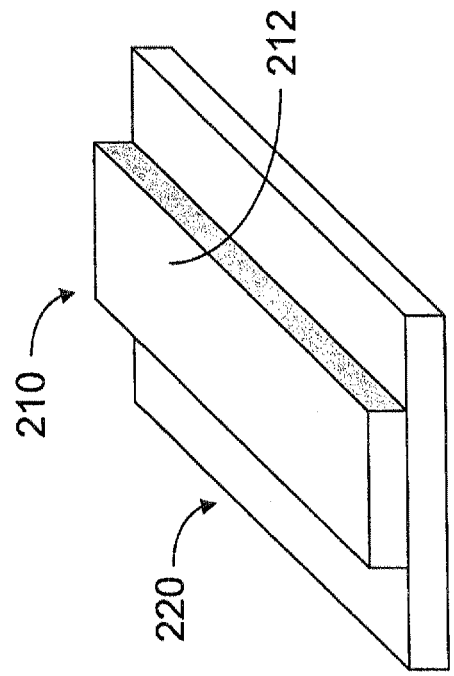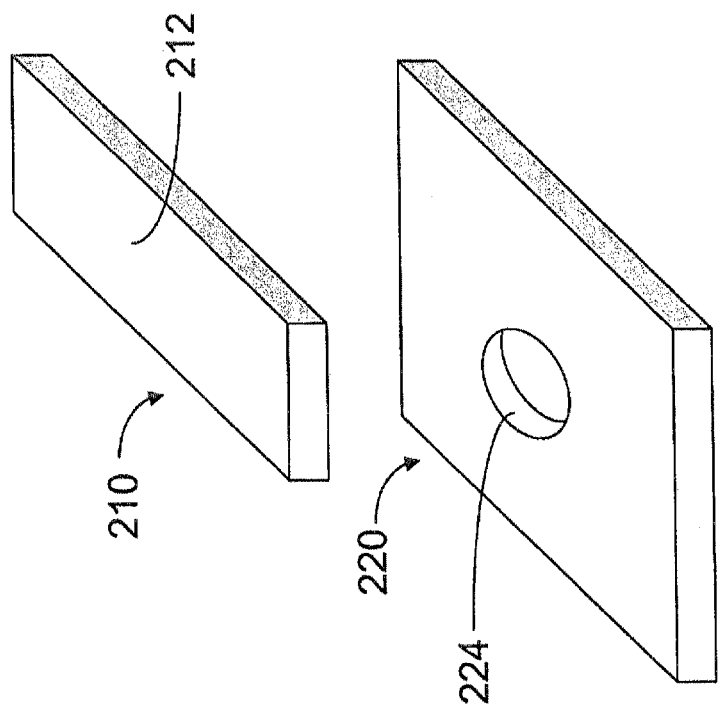
Fig. 5B
Fig. 5A

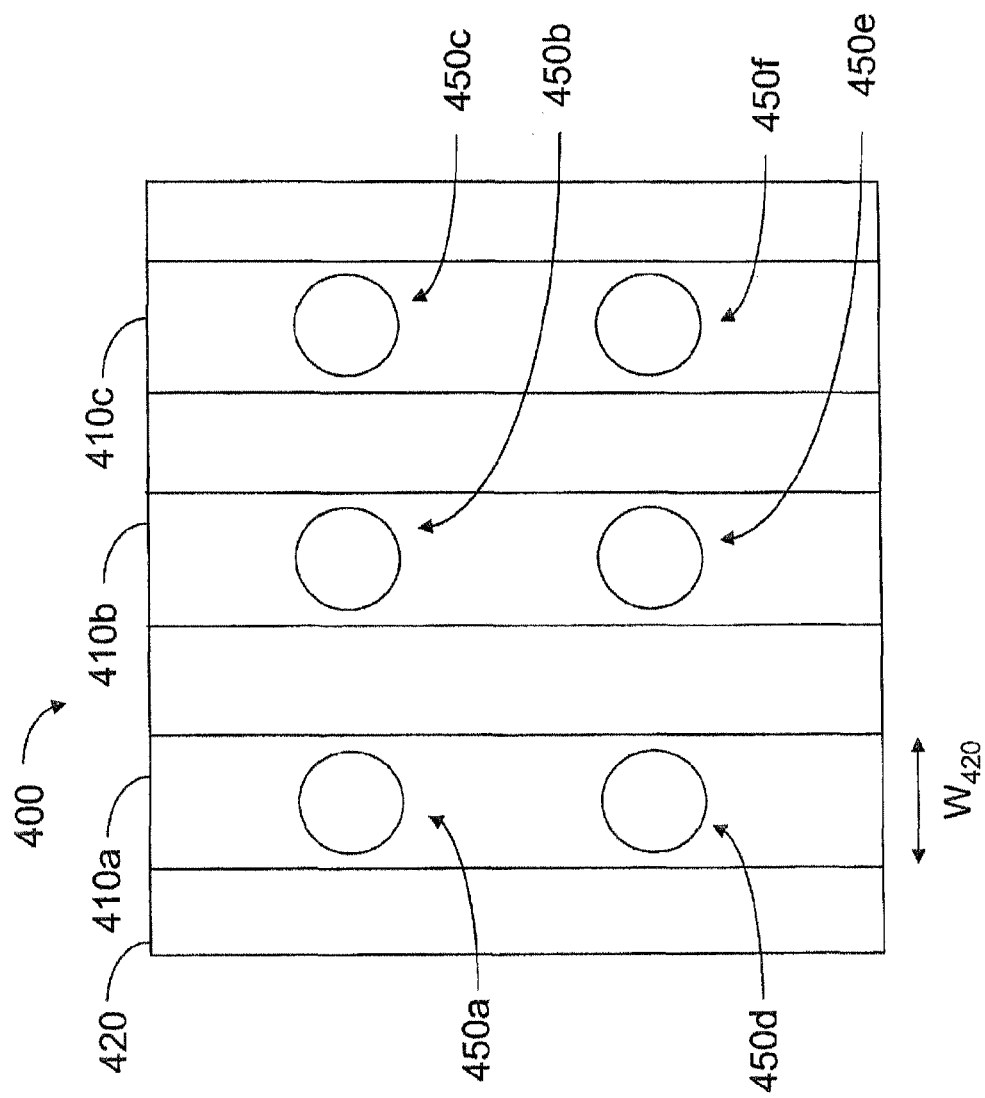

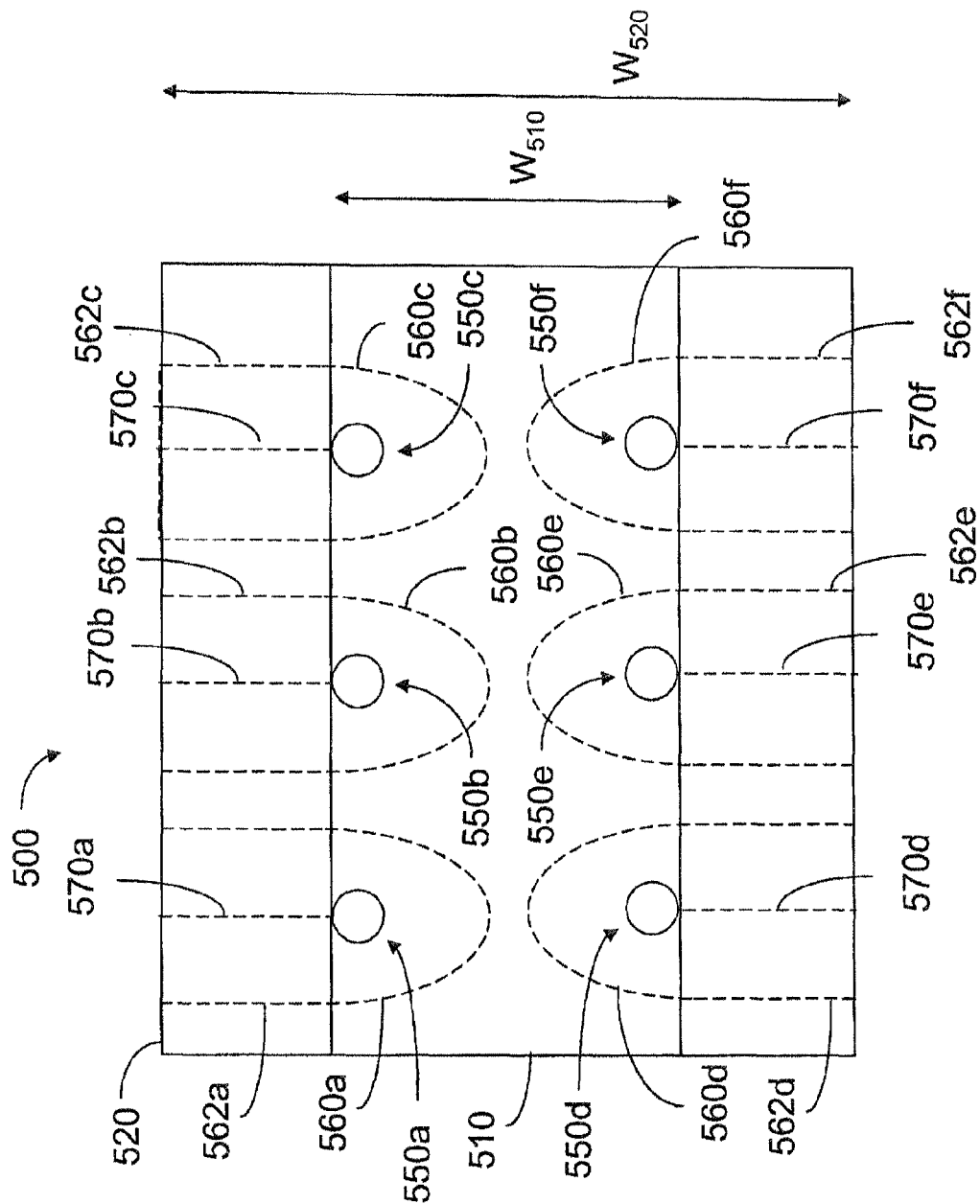

FABRIC PROSTHESIS FOR REPAIRING A TISSUE WALL DEFECT IN PROXIMITY OF A TUBE-LIKE STRUCTURE

RELATED APPLICATIONS

This Application claims priority under 35 U.S.C. §119(e) to U.S. Provisional Application Ser. No. 61/413,073, entitled "FABRIC PROSTHESIS FOR REPAIRING A TISSUE WALL DEFECT IN PROXIMITY OF A TUBE-LIKE STRUCTURE" filed on Nov. 12, 2010, which is herein incorporated by reference in its entirety.

FIELD

The invention relates to a fabric prosthesis for repairing a tissue wall defect in proximity of a tube-like structure.

BACKGROUND

Various prosthetic devices have been proposed to reinforce tissue walls and to close tissue wall defects in proximity to a tube-like structure, such as the spermatic cord in connection with an inguinal hernia repair. Such soft tissue repair implants may include a mesh fabric with an opening to receive the tube-like structure and a barrier layer extending across a surface of the mesh fabric. A representative commercial device includes the BARD SPERMATEX inguinal repair prosthetic.

SUMMARY

In an illustrative embodiment, an implantable prosthesis for repairing a tissue wall defect near a tube-like structure is provided. The implantable prosthesis includes a first fabric layer, a second fabric layer, and a passageway extending through the first and second fabric layers having an opening adapted to receive a tube-like structure. A cross-sectional area of the passageway extending through the first fabric layer is smaller than a cross-sectional area of the passageway extending through the second fabric layer. In one variation, a barrier is provided at the passageway through the first fabric layer. The barrier may constitute a composite with the fabric of the first fabric layer, or jut out from an edge of the first fabric layer defining an opening through the first fabric layer. The first and second fabric layers may be configured in the form of a patch.

In another illustrative embodiment, an implantable prosthesis for repairing a tissue wall defect near a tube-like structure is provided. The implantable prosthesis includes a first fabric layer, a second fabric layer, and a passageway extending through the first and second fabric layers that is adapted to receive a tube-like structure. The first fabric layer is adapted to obstruct contact between the tube-like structure and an edge of the second fabric layer defining the passageway through the second fabric layer. In one variation, the passageway through the first fabric layer has a cross-sectional area smaller than the cross-sectional area of the passageway through the second fabric layer. A barrier may be provided at the passageway through the first fabric layer. The barrier may constitute a composite with the fabric of the first fabric layer, or jut out from an edge of the first fabric layer defining an opening through the first fabric layer. The first and second fabric layers may be configured in the form of a patch.

In another illustrative embodiment, an implantable prosthesis for repairing a tissue wall defect near a tube-like structure is provided. The implantable prosthesis includes a first fabric layer, a second fabric layer, and a passageway through the first and second fabric layers adapted to receive a tube-like structure. The first and second fabric layers are stacked together, with each layer having an inferior edge, superior edge, medial edge, and lateral edge, and respective medial and lateral edges being substantially coincident. The inferior edge and superior edge of the first fabric layer is spaced inwardly from the respective inferior and superior edges of the second fabric layer. In one variation, the passageway through the first fabric layer has a cross-sectional area smaller than the cross-sectional area of the passageway through the second fabric layer. A barrier may be provided at the passageway through the first fabric layer. The barrier may constitute a composite with the fabric of the first fabric layer, or jut out from an edge of the first fabric layer defining an opening through the first fabric layer. The first and second fabric layers may be configured in the form of a patch.

In yet another illustrative embodiment, a method of manufacturing an implantable prosthesis for repairing a tissue wall defect near a tube-like structure is provided. The method includes joining together a first fabric layer and a second fabric layer, forming an opening in the second fabric layer that is adapted to receive a tube-like structure, providing a barrier with the first fabric layer, and forming a passageway through the barrier that is adapted to receive a the tube-like structure, wherein a cross-sectional area of the passageway is smaller than a cross-sectional area of the opening in the second fabric layer. In a variation, an opening is formed in the first fabric layer that aligns with the opening in the second fabric layer, where the opening is similarly sized, or smaller then, the opening in the second fabric layer. In one variation, the passageway through the first fabric layer has a cross-sectional area smaller than the cross-sectional area of the passageway through the second fabric layer. The barrier may constitute a composite with the fabric of the first fabric layer, or jut out from an edge of the first fabric layer defining an opening through the first fabric layer. The first and second fabric layers may be configured in the form of a patch.

The foregoing is a non-limiting summary of the invention, which is defined by the attached claims. Other aspects, embodiments, features will become apparent from the following description.

BRIEF DESCRIPTION OF THE DRAWINGS

The accompanying drawings are not intended to be drawn to scale. In the drawings, each identical or nearly identical component that is illustrated in various figures is represented by a like descriptor. For purposes of clarity, not every component may be labeled in every drawing.

The advantages and features of this invention will be more clearly appreciated from the following detailed description, when taken in conjunction with the accompanying drawings.

FIG. 1A is a perspective view of an embodiment of a prosthesis according to aspects of the invention;

FIG. 1B is a top view of the prosthesis of FIG. 1A;

FIG. 1C is a sectional view of the prosthesis of FIG. 1A along lines 1C of FIG. 1B;

FIG. 2A is a perspective view of another embodiment of a prosthesis according to aspects of the invention;

FIG. 2B is a top view of the prosthesis of FIG. 1B;

FIG. 2C is a sectional view of the prosthesis of FIG. 2A along lines 2C of FIG. 2B;

FIG. 4C is a view of a manufacturing step where a barrier is applied;

FIG. 4D is a view of a manufacturing step with an opening formed in the barrier;

FIG. 5A is a view of a manufacturing step illustrating two fabric layers with one fabric layer having an opening formed therein;

FIG. 5B is a view of a manufacturing step where the fabric layers are joined together;

FIG. 6A is a top view of a monolith fabric co-knit;

FIG. 7 is a top view of another monolith fabric co-knit.

DETAILED DESCRIPTION OF EMBODIMENTS

Figure 3:
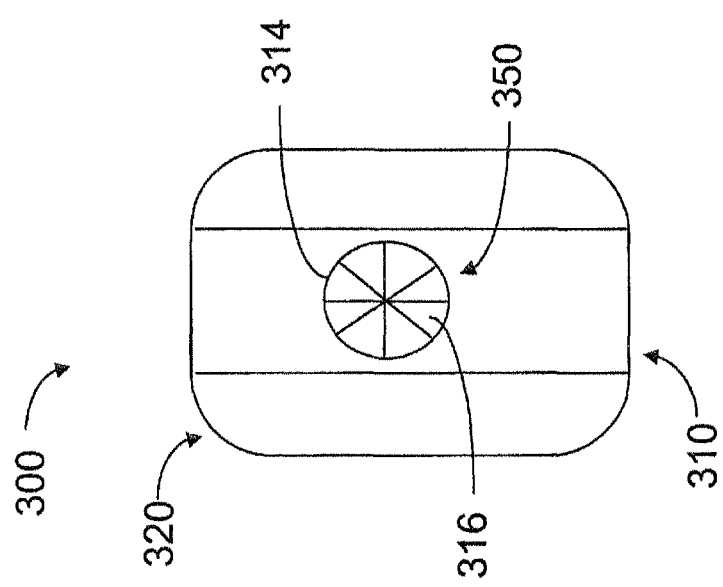
FIG. 3 is a top view of another embodiment of a prosthesis according to aspects of the invention.

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. It should be appreciated, then, that the various concepts and embodiments introduced above and those discussed in greater detail below may be implemented in any of numerous ways, as the disclosed concepts and embodiments are not limited to any particular manner of implementation. In addition, it should be understood that aspects of the invention may be used alone or in any suitable combination with other aspects of the invention.

The present disclosure relates to implantable prostheses for treating a soft tissue defect and to methods of manufacturing such devices. Although described in connection with a prosthetic device for repairing an inguinal hernia, the implantable prostheses are not so limited and may be used in other applications particularly where a tissue wall defect undergoing treatment is proximate a tube-like structure. As a further example, and without limitation, such implantable prostheses may have application in the repair of a hiatal hernia where the esophagus is proximate the defect.

In a representative embodiment, an implantable prosthesis is in the form of a dual fabric-layer patch. The two fabric layers are positioned adjacent one another, with coincident openings in both fabric layers forming a passageway that is adapted to receive a tube-like structure, such as the spermatic cord when the implantable prosthesis is intended for repair of an inguinal hernia. The portion of the passageway through the first fabric layer is sized and shaped to obstruct or otherwise limit contact between the tube-like structure and the edge of the opening defined by the second fabric layer. The portion of the passageway through the first fabric layer may be characterized by a cross-sectional area that is smaller than a cross-sectional area defined by the opening through the second fabric layer, such that to the more narrowly dimensioned opening in the first fabric layer assists in isolating or precluding the tube-like structure from coming into contact with the edge of the opening defined by the second fabric layer. The first fabric layer may be configured so that the edge of the opening extending through the first fabric layer is in the form of a barrier to adhesion, erosion or integration with the tube-like structure. For example, and without limitation, the edge of the opening through the first fabric layer may include a resorbable polymer barrier, such as a hydrogel or other gelatinous material. The resorbable polymer barrier may project from the edge of the first fabric layer defining the opening, and/or be embedded at least partially within the first fabric layer and together therewith define the portion of the passageway through the first fabric layer. The passageway and/or openings through the fabric layers may have any suitable dimension or shape including, without limitation, a cross-sectional shape that is circular, oval or elliptical. Further, the passageway and/or openings need not extend normal to the fabric layers but may take any pathway through the prosthesis from the outer surface of the first fabric layer to the oppositely disposed outer surface of the second fabric layer.

In one arrangement, the openings through the first and second fabric layers may be similarly sized with the resorbable polymer barrier narrowing the portion of the cord passageway through the first fabric layer. In another arrangement, an opening through a first fabric layer/bioabsorbable polymer composite constitutes the portion of the passageway through the first fabric layer, such portion of the passageway has a cross-sectional area that is smaller than a cross-sectional area of an opening through the second fabric layer.

A bioactive agent, such as an analgesic, antibiotic, anesthetic or anti-inflammatory agent, may be loaded directly and/or via microspheres into the bioabsorbable polymer barrier and/or first fabric layer/bioabsorbable composite. In addition, or alternatively, a bioactive agent may be coated onto or otherwise integrated with one or both of the first and second fabric layers.

The two fabric layers may be positioned directly against one another, or one or more intermediate layers may be located therebetween. Alternatively, one or more additional layers may be positioned above and/or below the fabric layers. The fabric layers are formed of a textile material that is biocompatible and suitable for implantation and repair of the targeted tissue wall. Representative fabrics include knitted, woven, braided, felted and/or non-woven structures. The first and second fabric layers may have the same or a different textile construction. Either fabric layer may be resorbable or non-resorbable, and the resorbability characteristics may vary at different sections of a layer. The first and second fabric layers may be characterized as laid one on top of the other, although any orientation of the fabric layers may be used as a reference (e.g., side-by-side). The fabric layers may be joined together during fabric formation, for example, layers that are knit may be co-knit together. Also, the fabric layers may be independently formed and then joined by stitching, fusing, adhesive bonding and/or other fabric layer uniting methodologies as should be apparent to one of skill in the art, The fabric layers may have the same or a different shape, and may have the same or a different size. In certain embodiments, the first and second fabric layers may have the same length but a different width, or a different width and the same length. The implantable prosthesis preferably is provided in the form of a patch with one fabric layer stacked upon the other fabric layer, directly or indirectly, although other configurations of the implantable prosthesis are contemplated as should be apparent to one of skill in the art. The implantable prosthesis may include more than two layers, and each layer of the implantable prosthesis need not have an opening that forms part of a passageway for receiving the tube-like structure. A slit may be formed in the implantable prosthesis, as-manufactured or by the surgeon, providing access to the passageway for the tube-like structure.

FIGS. 1A-1C and 2A-2C illustrate embodiments of implantable prostheses 100 and 200 suitable for repair of an inguinal hernia. The prostheses are shown in the form of a patch having a first fabric layer and a second fabric layer, where the second fabric layer may be configured for tissue infiltration and may be arranged so as to provide appropriate physical properties to satisfactorily mend the defect (e.g., burst strength). A passageway extends through each of the implantable prostheses that is adapted to receive a spermatic cord, and a slit may be provided to facilitate access to the passageway. The portion of the passageway extending through the first fabric layer is narrower than the portion of the passageway running through the second fabric layer. The narrower first fabric passageway portion obstructs or otherwise reduces the likelihood of contact between the spermatic cord and an edge of the second fabric layer defining the passageway portion therethrough.

As shown in FIGS. 1A-1C, prosthesis 100 includes a bioabsorbable polymer barrier 116 that extends from an edge 114 of an opening through the first fabric layer 110 and constitutes the portion of the passageway 150 through the first fabric layer that receives the spermatic cord. As depicted, the barrier 116 may jut away from the edge of the first fabric layer and may act as a bumper, isolating the spermatic cord both from the edge 114 of the first fabric layer 110 and the adjacent edge of the second fabric layer 120 defining the passageway extending through the second fabric layer. An inner edge 118 of the barrier 116 defines an opening that is smaller than the opening formed by the edge 114 of the first fabric layer 110, as well as the opening through the second fabric layer 120. Although illustrated with a ring-shape that tracks the contour of the opening in the first fabric layer 110, other shapes of the barrier are contemplated as should be apparent to one of skill in the art. In this embodiment, although not required, an edge 114 defining the opening in the first fabric layer 110 is aligned substantially flush with an edge 124 defining the opening in the second fabric layer 120; that is, a width $W_{114}$ defined by edge 114 is about equal to a width $W_{124}$ defined by edge 124. An extension of the barrier may run along some or all of the first fabric layer defining slit 130.

In addition to a barrier defining the portion of the passageway 150 extending through the first fabric layer, one or more portions of the surface of the first fabric layer and, optionally, one or more outer edges of the first fabric layer may include a barrier. For example, and without limitation, a bioabsorbable polymer barrier may coat and/or impregnate into suitable surface regions of the first fabric layer. Thus, all or only selected portions of first fabric layer in the patch shown in FIGS. 1A-1C, may be impregnated with a bioabsorbable polymer barrier. A barrier might be applied just to selected region(s) of the surface of the first fabric layer. The barrier at localized areas of the first fabric may be the same material as that which forms the barrier at the passageway through the first fabric layer, may be a different material or a different form of the same material. In connection with an inguinal hernia repair prosthetic, the barrier may be applied along those aspects of the surface of the first fabric layer contemplated as coming, or potentially coming, into contact with the spermatic cord. Areas of the surface of the first fabric layer not expected to come into contact with the spermatic cord may be left free of a barrier, so as to enhance the overall tissue ingrowth capabilities of the prosthetic device. The barrier may be a gelatinous material that will gellate after implantation and activation by body fluids. In some cases, portions of a barrier material may be disposed along both surfaces of the fabric patch.

For the prosthesis 200 shown in FIGS. 2A-2C, the barrier may be a composite of bioabsorbable polymer and the fibers forming the first fabric layer 210; that is, the bioabsorable polymer may be embedded at least partially in an edge region 214 of the first fabric layer 210 defining the opening through the first fabric layer. The openings of the first and second fabric layers are coincident to form the passageway 250 through the prosthesis receiving the spermatic cord. A cross-sectional area of the opening defined by the edge 214 of the first fabric layer 210 is smaller than a cross-sectional area of the coincident opening of the second fabric layer 220, so that contact between the spermatic cord and an edge of the second fabric layer 220 is impeded. Dashed lines in FIG. 2B signify the location of edge 224 which defines the opening in the second fabric layer. This arrangement is different from implantable prosthesis shown in FIGS. 1A-1C where the size of the openings in the first and second fabric layers are about equal.

The implantable prosthesis 100, 200 for inguinal hernia repair shown in FIGS. 1A-1C and 2A-2C may be characterized by a lateral edge L, a medial edge M, an inferior edge I and a superior edge S. While medial and lateral edges of the first and second fabric layers are substantially coincident (e.g., or substantially flush), the inferior and superior edges of the first fabric layer are spaced inwardly from the inferior and superior edges of the second fabric layer. Such spacing gives rise to a width $W_{110}$, $W_{210}$ of the first fabric layer, at its widest point between inferior and superior edges, that is narrower than a width $W_{120}$, $W_{220}$ of the second fabric layer, at its widest point between inferior and superior edges. The portions of the second fabric layer not covered by the first fabric layer may be particularly suited for tissue ingrowth. While the prosthesis 100, 200 is depicted as rectangular, the shape of the prosthesis is not so limited, nor is the shape of the individual fabric layers, each of which can be formed into other shapes appropriate for the intended application.

A slit optionally formed through the prosthesis for access to passageway 150 may similarly include a barrier that extends inward from an edge of a fabric layer defining the slit. One of skill in the art will appreciate that other arrangements of a slit in the first and second fabric layers are contemplated, including where a layer or layers forming one side of the slit may overlay the layer or layers forming the other side of the slit, providing a selectively openable slit. Although shown as having a linear shape and extending axially, the slit may have other configurations and may extend in different directions as should be apparent to one of skill in the art. For some embodiments, a slit is formed in a lateral region of the fabric patch, for example, through the lateral edge extending to the passageway.

The body of the first fabric layer may be impregnated with a gelatinous material that coats fibers of the fabric and fills gaps between the fibers. In the embodiment of FIGS. 2A-2C, for example, fabric body 212 has a gelatinous material permeated throughout. It should be appreciated that for certain embodiments, an additional barrier may be provided on any suitable portion of a fabric layer, such as further gelatinous material, other polymeric barriers (e.g., ePTFE)

and/or other suitable substance(s). For example, in the embodiment of FIGS. 2A-2C, an extra gelatinous material (not expressly shown) may be layered on to the already coated or impregnated fabric body 212 of the first fabric layer 210 to provide a barrier that extends further inward into the passageway 250.

In certain embodiments, a barrier defining the passageway in the first fabric layer may be arranged to cover at least a portion of the opening in the second fabric layer upon entry of the tube-like structure through the first fabric layer, serving to isolate the tube-like structure from edges of the passageway. The composition of the barrier may effect its ability to deform, bend or otherwise extend to cover the opening through the second fabric layer. For example, a fiber reinforced barrier may be mechanically stiff and, hence, resist covering the opening through the second fabric layer; though, a fiber reinforced barrier may still deform. Conversely, a barrier that includes only a hydrogel or other gelatinous material in the absence of fibrous material may be more flexible and likely to respond to the presence of the tube-like structure. Further, the magnitude of radial extension, or thickness, may influence the ability of a barrier to adjust towards the second fabric layer. For example, a thicker barrier may be more prone to movement as compared to a barrier that juts out only a slight distance. Also, the barrier may be modified to facilitate extendability towards the second fabric layer. For example, and without limitation, relaxation slits formed in the barrier may lessen resistance to movement of the barrier in response to the presence of the tube-like structure. In the implantable prosthesis 300 shown in FIG. 3, a barrier 314 at the first fabric layer 310 may include a plurality of flaps 316. Such flaps are adapted to fold inward as a tube-like structure is introduced into the passageway 350. The ends of the folded flaps may reach and cover some or all of the opening through the underlying second fabric layer 320, isolating the tube-like structure from contact with the second fabric layer.

Turning now to a discussion of representative components of the implantable prostheses, fibers of the first fabric layer preferably are resorbable, although non-resorbable fibers also are contemplated. Non-limiting examples of materials for forming a resorbable first fabric layer include resorbable polyesters such as polyglycolic acid (PGA), polylactic acid (PLA), poly(lactic-co-glycolic acid) (PLGA), polydioxanone (PDO), polycaprolactone (PCL), any resorbable polyester fiber, polyhydroxyalkanoate (PHA), and any other resorbable polyester, as well as collagen, calcium alginate and combinations of any of the foregoing. Fibers that make up the second fabric layer preferably are non-resorbable, or more slowly resorbable than fibers in the first fabric layer. The second fabric layer may be formed of polypropylene (PP), polyethylene, polyester, or other polymers having application in soft tissue repair fabrics. When implanted, the second fabric layer may be configured to promote tissue ingrowth into interstices of the fabric and around the fabric structure, and may be arranged with properties suitable for repairing the defect (e.g., burst pressure). The fibers forming the fabric layers may be monofilament or multifilament.

The barrier may include any suitable gel, foam, film or membrane. In certain embodiments, the barrier is applied in solution to the first fabric layer, so as to impregnate the fibrous structure and/or to form a cast extension of the first fabric layer that constitutes a portion of the passageway through the first fabric layer. The barrier may be resorbable and may resist tissue adhesions to the fabric patch. Representative materials for forming the barrier include hyaluronic acid (e.g., chemically modified sodium hyaluronate), carboxymethyl cellulose (CMC), polyethylene glycol (PEG), collagen, omega fatty acid or combinations/mixtures thereof. Such materials may be applied to the fabric in the form of a gelatinous material, such as but not limited to, a hydrogel. In an embodiment, a resorbable adhesion barrier includes a mixture of carbodiimide modified sodium hyaluronate-carboxymethyl cellulose (HA/CMC). In this case, the carbodiimide modification forms N-acyl urea derivatives of polysaccharides that become water insoluble, yet hydrogel-forming. In another embodiment, a barrier includes a PEG-based hydrogel which is formed, for example, from a copolymer of PEG, trimethylenecarbonate (TMC) and lactate (LA) end capped with acrylate esters.

A representative embodiment of the implantable prosthesis includes a two-layer fabric prosthesis comprising a PP monofilament knit on one side, a narrower strip of PGA multifilament knit on the other side, with the two knit layers joined by PGA connecting yarns. The layers may be co-knit on a four guide bar, double needle bar machine. A hole sized between about ⅜ inches and about ¾ inches in diameter is punched through the first and second fabric layers. A bioresorbable polymer barrier formed from a mixture of chemically modified sodium hyaluronate (HA), carboxymethyl cellulose (CMC), and a PEG-based hydrogel is cast onto the PGA fabric side of the prosthesis, impregnating the PGA fabric and forming a plug in the punched opening through the PGA fabric. A smaller opening, for example, approximately ½ inch in diameter, is formed through the barrier plug, creating a barrier bounded passageway for the spermatic cord through the first PGA fabric layer that extends into the wider punched opening in the second PP fabric layer. The wall thickness of the barrier from an inner edge of the PGA body to the inner edge of the barrier may be, for example, approximately ⅛ inch. Upon implantation, the barrier resorbs from the implant site within a certain time period, for example, 7-30 days. In a representative embodiment where the first fabric layer is made up of PGA fibers, resorption of the PGA layer may occur between about 50 and about 80 days. Upon resorption of the barrier and PGA fibers, the non-resorbable PP knit remains and permits tissue in-growth. One of skill in the art will appreciate that a resorbable barrier and first fabric layer may be selected in accordance with a desired resorption time.

Figure 4B:
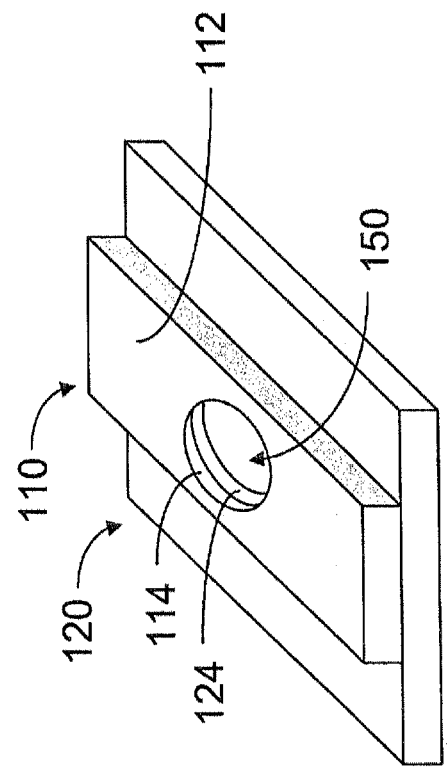
FIG. 4B is a view of a manufacturing step where openings are formed in the fabric layers.
Figure 4A:
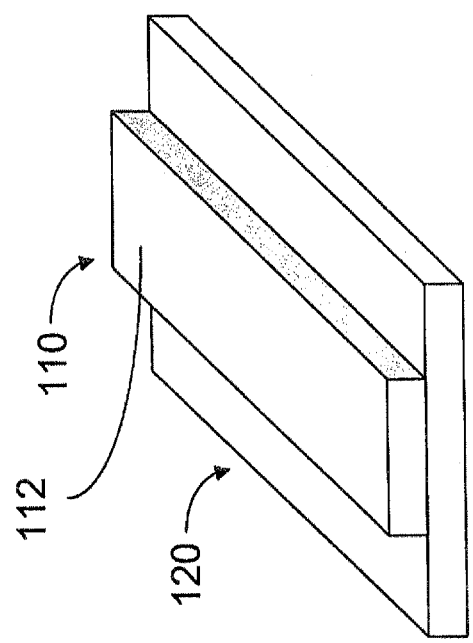
FIG. 4A is a view of a manufacturing step where two fabric layers are joined together.

FIGS. 4A-4D disclose a process for manufacturing the implantable prosthesis shown in FIGS. 1A-1C. A first fabric layer 110 and a second fabric layer 120 are joined together in FIG. 4A, such as by co-knitting. FIG. 4B depicts aligned openings 150 that have been formed through the first and second fabric layers. The aligned openings 150 may be formed simultaneously through the first and second fabric layers, for example, by punching respective openings through the two layers; or, such openings may be formed separately in each of the fabric layers. As shown in FIG. 4C, a barrier 116 is applied to the opening of the first fabric layer 110, forming a barrier plug filling the opening. For example, and without limitation, the barrier plug may be formed by immersing first fabric layer 110 into an appropriate barrier solution, as discussed in more detail below.

As shown in FIG. 4D, an opening is made in the barrier plug, leaving a barrier 116 ring extending from the edge of the opening previously formed in the first fabric layer. The opening in the barrier may be formed, for example, by punching or cutting through the barrier plug. Alternatively, an insert could be provided within the opening while the barrier is cast, blocking incorporation of the barrier in a desired area (e.g., such as through the center of the opening in the first fabric layer). The edge 118 of the opening formed through the barrier 116 constitutes the portion of the passageway through the first fabric layer. A cross-sectional area defined by the passageway portion through the barrier is smaller than a cross-sectional area of the opening that had been formed through the underlying second fabric layer 120. A slit 130 may be formed through the first and second layers to facilitate entry of a tube-like structure into the passageway 150.

Figure 4E:
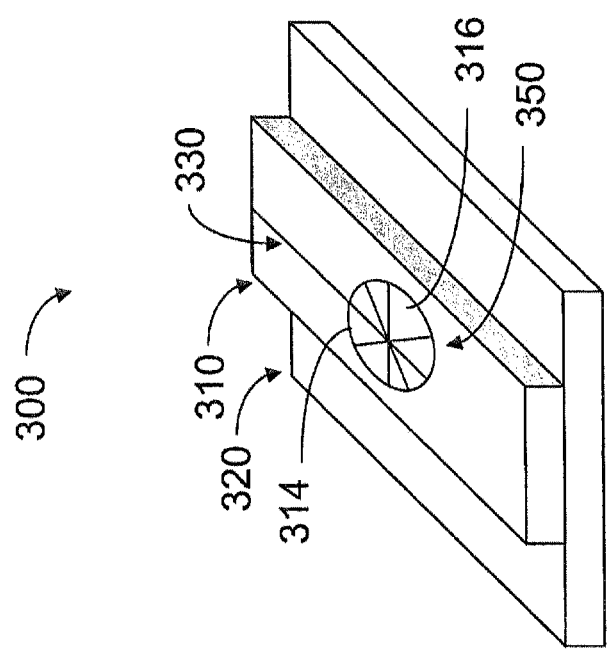
FIG. 4E is a view of a manufacturing step where a plurality of flaps are formed in the barrier.

To form the prosthesis 300 shown in FIG. 4E, rather than punching a hole through the barrier, a plurality of flaps 316 are formed at an opening in the passageway 350 of first fabric layer 310. Here, the barrier plug is cut into wedge-shaped flaps, with a suitably sized slit 330 also formed. In certain embodiments, a small hole may be provided at the junction of the flap tips. When a tube-like structure is placed into the passageway 350, the flaps 316 may fold inwardly from the opening of the first fabric layer toward the underlying opening of the second fabric layer forming a barrier between the tube-like structure and at least some part of the edge defining the opening through the second fabric layer. It can be appreciated that any suitable configuration of flaps, and method of forming the same, may be employed.

Figure 5D:
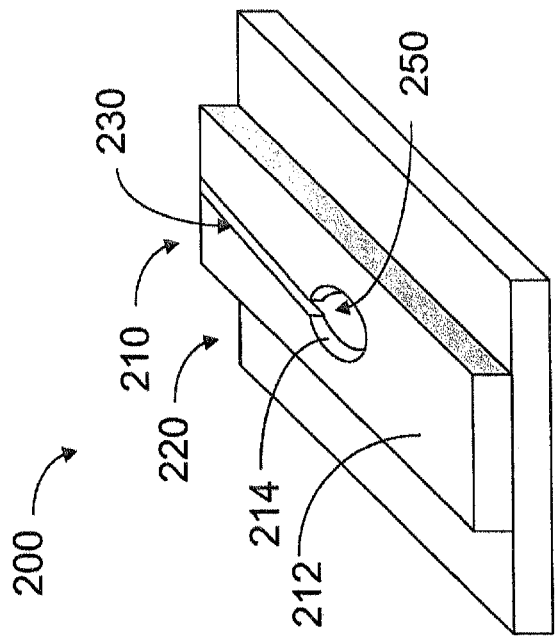
FIG. 5D is a view of a manufacturing step where a slit formed through the fabric layers.
Figure 5C:
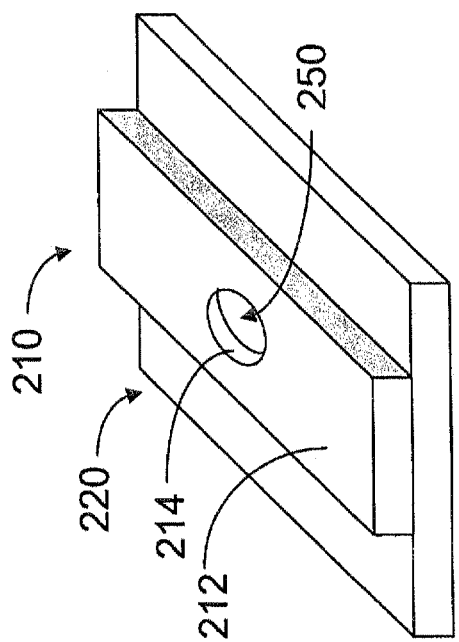
FIG. 5C is a view of a manufacturing step where an opening is formed in the first fabric layer.

Turning to FIGS. 5A-5D, a process for making the implantable prosthesis depicted in FIGS. 2A-2C is described. A first fabric layer 210 is joined to a second fabric layer, the second fabric layer previously having been provided with an opening defined by edge 224. First and second fabric layers may be joined together, for example, by stitching, fusing, adhesive bonding, or another arrangement for uniting fabric layers together as should be apparent to one of skill in the art. A bioresorbable polymer barrier is cast to the first fabric layer 210, for example, by suspending the first fabric layer into a container having a barrier solution, described further below in FIGS. 6A-6B. The barrier coats the fibers within the body 212 of the first fabric layer and fills gaps between the fibers, forming a resorbable polymer fiber/barrier composite. As depicted in FIG. 5C, an opening defined by edge 214 is then formed in the barrier impregnated first fabric layer that is smaller than the opening through the second fabric layer. The opening in the composite barrier/first fabric layer and the second fabric layer combine to form a passageway through the prosthesis for receiving a cord-like structure. A slit 230 may be formed through the fabric layers, as shown in FIG. 5D, to provide access to the passageway for the cord-like structure.

Clusters of implantable soft-tissue repair patches may be manufactured together as a larger fabric composite, with individual prostheses being separately removed during the finishing stages. For example, FIG. 6A illustrates a large fabric co-knit 400 having several narrow strips of fabric layers 410a, 410b and 410c (e.g., PGA layers) spaced about an underlying fabric layer 420 (e.g., PP layer). In certain embodiments, as shown in FIG. 6A, passageways 450a-450f for receiving a spermatic cord are pre-cut or pre-punched through the fabric co-knit prior to casting of the fabric layers 410a-410c in a barrier solution. In other embodiments, openings may be formed only in the larger fabric layer 420 prior to casting of the first fabric layers 410a-410c in the barrier solution. Openings are then subsequently formed in the barrier impregnated fabric layers 410a-410c to create passageways 450a-450f.

Figure 6B:
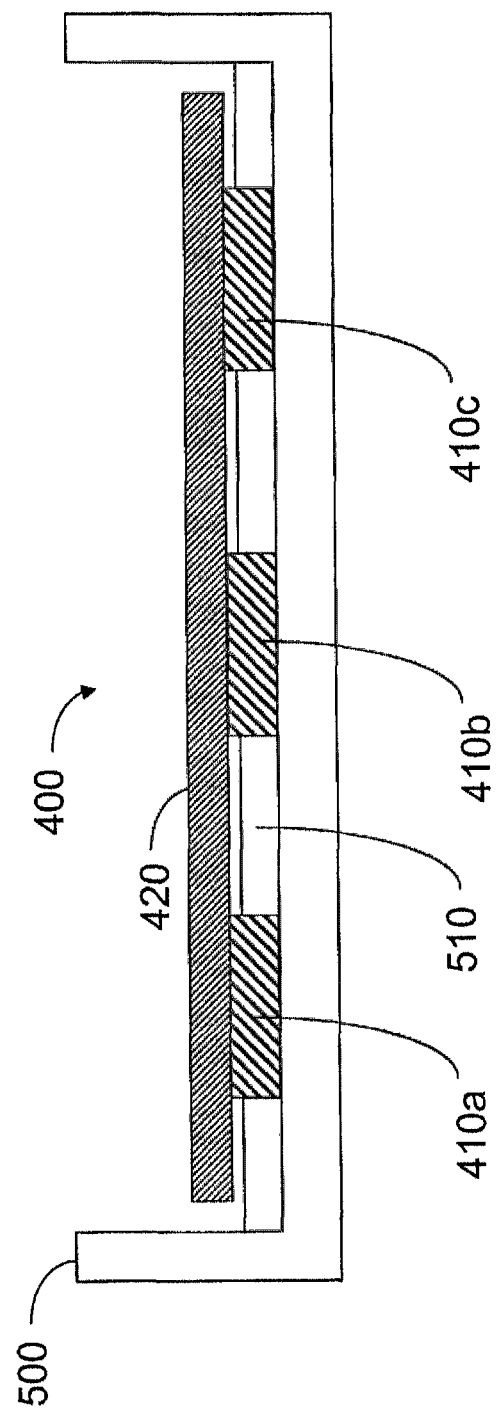
FIG. 6B is a view of a monolith fabric co-knit immersed in a barrier solution.

As illustrated in FIG. 6B, a casting container 500 is filled with a barrier solution 510. An exemplary, yet non-limiting barrier solution includes a hyaluronic acid and carboxymethyl cellulose solution. Inverted fabric co-knit 400 is immersed into the barrier solution 510. The monolith fabric is maintained in the barrier solution for a sufficient time for the barrier to permeate through fabric layers 410a-410c. In certain embodiments, as shown in FIG. 6B, the depth of the barrier solution 510 in the casting container 500 is less than the thickness of the fabric layers 410a-410c. While aspects of the invention are not so limited, this arrangement ensures that the fabric layer 420 is not impregnated with barrier solution, permitting the pores to remain open and available for tissue ingrowth upon implantation. A spacing between fabric strips 410a-410c may be chosen to ensure that fabric layer 420 does not sag between the fabric strips and come into contact with the barrier solution 510. It is recognized that in certain embodiments it may be desirable for some or all of the fabric layer 420 to be immersed in the barrier solution. As discussed above, in some embodiments a barrier may be located along both surfaces of an implantable fabric. In some embodiments, the barrier solution 510 may include one or more photo initiators and/or catalysts disposed within a suitable buffer, such as but not limited to, potassium phosphate and triethanolamine. In cases where the barrier solution 510 contains a photo initiator, the barrier solution may be subjected to photo initiation, such as by exposure to UV or visible light.

After the fabric monolith 400 has been removed from the container, and the barrier is sufficiently stable for further finishing, openings may be formed through the barrier (whether in the form of a film or a composite of barrier/fabric) consistent with any of the foregoing embodiments. The monolith may be cut widthwise and lengthwise, as appropriate, to form individual prosthetic devices which may then be packaged. Implantable prostheses described herein may be sterilized at any appropriate point during the manufacturing or packaging phases.

A different monolith 500 for manufacturing together clusters of implantable fabric patches is depicted in FIG. 7. The monolith includes a resorbable fabric strip 510 (e.g., PGA layer) extending across an underlying more slowly resorbable or permanent fabric layer 520 (e.g., PP layer). As shown, the fabric strip 510 is narrower than the underlying more slowly resorbable or permanent fabric layer 520 ($W_{520} > W_{510}$). In contrast to the just described monolith, here the medial to lateral length of the implant is formed transverse to the narrower fabric strip. So, unlike the implant formed by the process described in connection with FIGS. 6A-6B, here the resorbable fabric layer does not run completely from medial edge to lateral edge. For example, as depicted, a lateral region of the more slowly resorbable or permanent fabric layer 520 does not include the resorbable fabric strip 510. Also as shown, the resorbable fabric strip 510 extends from an inferior edge to a superior edge of a medial region of the more slowly resorbable or permanent fabric layer 520. In the illustrated embodiment, the keyhole 550a-550f is provided through a composite of the resorbable layer 510 and the more slowly resorbable or permanent layer 520, and the surrounding medial portion 560a-560f of the implant also includes the composite layers. However, the slit 570a-570f extends along the portion of the implant 562a-562f that only includes the more slowly resorbable or permanent fabric.

In use, a spermatic cord extending through the keyhole 550a-550f will be draped over the medial portion 560a-560f which, as described previously, may have a surface configured as a barrier (e.g., barrier covering and/or impregnating surface of medial portion). As in previous embodiments, the passageway for the spermatic cord may be formed so that a smaller opening extends through the resorbable fabric layer 510 as compared to the opening through the more slowly resorbable or permanent fabric layer 520. The size and relative positioning of the composite layers along the implant may be varied from that shown as should be apparent to one of skill in the art In a representative repair of an inguinal hernia, the implantable prosthesis is positioned such that the second fabric layer of the patch lays against the abdominal wall with the first fabric layer of the patch facing away from the tissue defect. The spermatic cord is routed through the passageway through the prosthesis, with the narrower opening through the first fabric layer assisting in isolating the spermatic cord from the second fabric layer on the opposite side. In embodiments where a barrier is provided at the opening in first fabric layer, and potentially also at surface regions of the first fabric layer, the barrier will gellate and provide a resorbable intermediary between the spermatic cord and the second fabric layer.

In certain embodiments, a bioactive agent (e.g., analgesic, antibiotic, anti-inflammatory, anesthetic) may be loaded into an absorbable microsphere and the microsphere containing the bioactive agent may, in turn, be dispersed into the barrier of the prosthesis. The bioactive agent is arranged to diffuse through the microsphere and then subsequently diffuse through the barrier, providing sustained release of the medicament. For example, microspheres formed from PGA which contain an analgesic drug may be incorporated in a hydrogel barrier. Microspheres can be formed from any suitable resorbable material, such as for example, PGA, PLA, PLGA, PDO, PCL, calcium alginate and/or combinations thereof. Once implanted, the analgesic elutes through the host microsphere, through the hydrogel matrix, and to the surrounding tissue. The size and composition of the microspheres may be chosen to achieve desired diffusion characteristics, particularly in view of the properties of the barrier into which they will be dispersed. In a representative embodiment, the microsphere and hydrogel barrier provide a release profile of about 2 to 10 days. One of skill in the art will appreciate that bioactive agent loaded microspheres may be incorporated into a barrier prior to application of the barrier to the first fabric layer or after the barrier has been applied to the first fabric layer. As should be apparent to one of skill in the art, a bioactive agent may also be loaded directly into the barrier without use of microspheres. Representative bioactive agents include, but are not limited to, analgesics, anti-fibrotic agents, anti-infective agents, anti-inflammatory agents, anti-oxidant agents, fibrosing agents, antibiotics and/or combinations thereof.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

It will be apparent that other embodiments and various modifications may be made to the present invention without departing from the scope thereof. For example, hernia patches having alternative shapes may also be contemplated within the scope of the present invention. Prosthetic patches for any type of hernia repair in addition to inguinal hernias are also considered, such as for example, hiatal hernia, femoral hernia, umbilical hernia, abdominal hernia, diaphragmatic hernia as well as for treatment of gastroesophageal reflux disease. The implantable prosthesis may be used in open or minimally-invasive procedures. The foregoing description of the invention is intended merely to be illustrative and not restrictive thereof. The scope of the present invention is defined by the appended claims and equivalents thereto.

What is claimed is:

1. An implantable prosthesis for repairing a tissue wall defect near a tubular structure, the prosthesis comprising:
   a first fabric layer including a first surface, a second opposed surface, and a first edge portion extending from the first surface to the second opposed surface and defining a length therebetween, the first edge portion defining a first opening, the first fabric layer also including a barrier that is connected to an integrated with the first edge portion along the length thereof, the barrier extending from and being co-planar with the first edge portion along the length thereof to form a continuous ring;
   a second fabric layer having a medial edge, a lateral edge, a superior edge and an inferior edge, the second fabric layer including a body portion constructed and arranged to cover and to repair an inguinal hernia defect, the second fabric layer including a second edge portion defining a second opening, the second opening registered with the first opening; and
   a passageway through the first and second layers that is adapted to receive a tubular structure, the passageway defined by an opening through the coplanar barrier in the first fabric layer and the second opening through the second fabric layer, wherein the coplanar barrier in the first fabric layer is adapted to obstruct contact between the tubular structure when received in the passageway and the second edge portion of the second fabric layer, wherein a region of the second fabric layer located on a medial side of the passageway is continuous between the superior edge and the inferior edge of the second fabric layer along a line extending tangent to a medial edge of the passageway.

2. The implantable prosthesis of claim 1, wherein a cross-sectional area of the passageway through the first fabric layer is smaller than a cross-sectional area of the passageway through the second fabric layer.

3. The implantable prosthesis of claim 1, wherein the barrier includes a gelatinous material.

4. The implantable prosthesis of claim 3, wherein the gelatinous material includes hyaluronic acid, carboxymethyl cellulose, polyethylene glycol, collagen, omega fatty acid, and mixtures thereof.

5. The implantable prosthesis of claim 1, wherein the barrier does not extend into the second opening.

6. The implantable prosthesis of claim 1, wherein a second barrier is further included in selected portions of the first surface of the first fabric layer and the second opposed surface of the first fabric layer.

7. The implantable prosthesis of claim 1, further including a plurality of bioactive agent loaded microspheres dispersed within the barrier.

8. The implantable prosthesis of claim 1, further including a slit extending from the passageway to an edge of the prosthesis.

9. The implantable prosthesis of claim 1, wherein a width of the first fabric layer is narrower than a width of the second fabric layer.

10. The implantable prosthesis of claim 1, wherein the first fabric layer is resorbable.

11. The implantable prosthesis of claim 1, wherein the second fabric layer is nonresorbable.

12. The implantable prosthesis of claim 1, wherein the first and second fabric layers are co-knit together.

13. The implantable prosthesis of claim 1, wherein the first and second fabric layers are in the form of a patch.

14. The implantable prosthesis of claim 1, wherein the first opening and the second opening are similarly sized.

15. The implantable prosthesis of claim 1, wherein a cross-sectional area of the first opening in the first fabric layer is smaller than a cross-sectional area of the second opening in the second fabric layer, the passageway running through the first and second openings.

16. The implantable prosthesis of claim 1, wherein the barrier is arranged to cover at least part of the passageway through the second fabric layer in response to the presence of the tubular structure in the passageway through the first fabric layer.

17. The implantable prosthesis of claim 1, wherein the lateral edge of the second fabric layer is not substantially flush with a lateral edge of the first fabric layer.

18. The implantable prosthesis of claim 1, wherein the second fabric layer has a medial region including a medial region inferior edge and a medial region superior edge, and the first fabric layer extends from the medial region inferior edge to the medial region superior edge of the second fabric layer.

19. The implantable prosthesis of claim 18, wherein the inferior edge and the superior edge of the medial region of the second fabric layer is substantially flush with a respective inferior edge and a superior edge of the first fabric layer.

20. The implantable prosthesis of claim 1, wherein the first and second fabric layers have respective medial and lateral edges that are substantially flush, and wherein an inferior edge and a superior edge of the first fabric layer are spaced inwardly from the inferior edge and the superior edge of the second fabric layer.

* * * * *

UNITED STATES PATENT AND TRADEMARK OFFICE
CERTIFICATE OF CORRECTION

PATENT NO.         : 9,504,549 B2
APPLICATION NO.    : 13/286929
DATED              : November 29, 2016
INVENTOR(S)        : Roger E. Darois et al.

Page 1 of 1

It is certified that error appears in the above-identified patent and that said Letters Patent is hereby corrected as shown below:

In the Claims

At Column 12, Line 12, Claim 1:
Replace "an" with –and–

Signed and Sealed this
Twenty-eighth Day of February, 2017

Michelle K. Lee
*Director of the United States Patent and Trademark Office*